(12) United States Patent
Ibrahim et al.

(10) Patent No.: US 12,023,010 B2
(45) Date of Patent: Jul. 2, 2024

(54) ACCESS VISUALIZATION SYSTEMS

(71) Applicant: AtriCure, Inc., Mason, OH (US)

(72) Inventors: Tamer Ibrahim, Danville, CA (US); Matthew Monti, Cincinnati, OH (US)

(73) Assignee: AtriCure, Inc., Mason, OH (US)

( * ) Notice: Subject to any disclaimer, the term of this patent is extended or adjusted under 35 U.S.C. 154(b) by 0 days.

(21) Appl. No.: 17/935,873

(22) Filed: Sep. 27, 2022

(65) Prior Publication Data

US 2023/0021205 A1 Jan. 19, 2023

Related U.S. Application Data

(62) Division of application No. 15/154,714, filed on May 13, 2016, now abandoned.

(60) Provisional application No. 62/160,997, filed on May 13, 2015.

(51) Int. Cl.
*A61B 1/313* (2006.01)
*A61B 1/00* (2006.01)
*A61M 29/00* (2006.01)

(52) U.S. Cl.
CPC .......... *A61B 1/313* (2013.01); *A61B 1/00087* (2013.01); *A61B 1/00154* (2013.01); *A61M 29/00* (2013.01)

(58) Field of Classification Search
CPC . A61B 1/313; A61B 1/00087; A61B 1/00154; A61M 29/00
See application file for complete search history.

(56) References Cited

U.S. PATENT DOCUMENTS

| | | | |
|---|---|---|---|
| 3,945,371 A | 3/1976 | Adelman | |
| 4,046,150 A | 9/1977 | Schwartz et al. | |
| 4,195,624 A | 4/1980 | Douglas | |
| 4,204,528 A * | 5/1980 | Termanini | A61B 1/3137 396/17 |
| 4,254,762 A | 3/1981 | Yoon | |
| 4,269,192 A | 5/1981 | Matsuo | |
| 4,335,713 A | 6/1982 | Komiya | |
| 4,386,602 A | 6/1983 | Sheldon et al. | |
| 4,566,438 A | 1/1986 | Liese et al. | |
| 4,567,882 A * | 2/1986 | Heller | A61B 1/0625 128/207.14 |
| 4,662,360 A | 5/1987 | O'Hara et al. | |
| 4,682,585 A | 7/1987 | Hiltebrandt | |
| 4,705,041 A * | 11/1987 | Kim | A61M 29/00 606/198 |
| 4,721,097 A | 1/1988 | D'Amelio | |
| 4,819,620 A * | 4/1989 | Okutsu | A61B 1/0623 600/114 |
| 4,858,001 A | 8/1989 | Milbank et al. | |
| 4,953,539 A | 9/1990 | Nakamura et al. | |

(Continued)

FOREIGN PATENT DOCUMENTS

CN 1520894 A 8/2004

OTHER PUBLICATIONS

U.S. Appl. No. 15/154,714, filed May 13, 2016 in the name of Ibrahim et al. Non-Final Office Action mailed Aug. 27, 2020.

(Continued)

*Primary Examiner* — John P Leubecker
*Assistant Examiner* — Jae Woo
(74) *Attorney, Agent, or Firm* — Levine Bagade Han LLP

(57) ABSTRACT

Methods and devices described herein facilitate improved access of locations within the body.

15 Claims, 7 Drawing Sheets

(56) References Cited

U.S. PATENT DOCUMENTS

| | | | |
|---|---|---|---|
| 4,981,482 A | * | 1/1991 | Ichikawa .............. A61M 25/06 |
| | | | 606/191 |
| 5,025,778 A | | 6/1991 | Silverstein et al. |
| 5,050,585 A | | 9/1991 | Takahashi |
| 5,112,308 A | | 5/1992 | Olsen et al. |
| 5,154,166 A | | 10/1992 | Chikama |
| 5,205,816 A | | 4/1993 | Dodson et al. |
| 5,217,001 A | | 6/1993 | Nakao et al. |
| 5,237,984 A | | 8/1993 | Williams, III et al. |
| 5,271,380 A | | 12/1993 | Riek et al. |
| 5,337,734 A | | 8/1994 | Saab |
| 5,354,302 A | | 10/1994 | Ko |
| 5,385,572 A | * | 1/1995 | Nobles .............. A61B 17/3417 |
| | | | 606/167 |
| 5,406,940 A | | 4/1995 | Melzer et al. |
| 5,514,074 A | | 5/1996 | Yabe et al. |
| 5,523,782 A | | 6/1996 | Williams |
| 5,685,856 A | | 11/1997 | Lehrer |
| 5,876,330 A | | 3/1999 | Grabover et al. |
| 6,007,484 A | | 12/1999 | Thompson |
| 6,120,494 A | * | 9/2000 | Jonkman .......... A61M 25/0606 |
| | | | 604/510 |
| 6,190,357 B1 | | 2/2001 | Ferrari et al. |
| 6,217,509 B1 | | 4/2001 | Foley et al. |
| 6,228,052 B1 | * | 5/2001 | Pohndorf .......... A61M 25/0017 |
| | | | 604/93.01 |
| 6,475,226 B1 | | 11/2002 | Belef et al. |
| 6,554,793 B1 | | 4/2003 | Pauker et al. |
| 6,592,604 B2 | | 7/2003 | Hess et al. |
| 6,752,756 B2 | | 6/2004 | Lunsford et al. |
| 6,893,442 B2 | | 5/2005 | Whayne |
| 6,989,018 B2 | | 1/2006 | Fogarty et al. |
| 7,001,404 B1 | | 2/2006 | Chin |
| 7,063,698 B2 | | 6/2006 | Whayne et al. |
| 7,300,448 B2 | | 11/2007 | Criscuolo et al. |
| 7,938,842 B1 | | 5/2011 | Chin |
| 7,981,133 B2 | | 7/2011 | Chin |
| 8,083,690 B2 | | 12/2011 | Peterson et al. |
| 8,512,231 B2 | | 8/2013 | Yamane |
| 9,808,598 B2 | | 11/2017 | Korkuch et al. |
| 2002/0022764 A1 | | 2/2002 | Smith |
| 2004/0160147 A1 | | 8/2004 | Bochner |
| 2005/0148818 A1 | | 2/2005 | Mesallum |
| 2005/0059890 A1 | | 3/2005 | Deal et al. |
| 2006/0009762 A1 | | 1/2006 | Whayne |
| 2006/0015006 A1 | | 1/2006 | Laurence et al. |
| 2006/0041270 A1 | | 2/2006 | Lenker |
| 2006/0200124 A1 | | 9/2006 | Whayne et al. |
| 2006/0206113 A1 | | 9/2006 | Whayne et al. |
| 2006/0235381 A1 | | 10/2006 | Whayne et al. |
| 2006/0235455 A1 | | 10/2006 | Oshida |
| 2006/0293646 A1 | | 12/2006 | Whayne et al. |
| 2007/0179472 A1 | | 1/2007 | Whittaker |
| 2007/0043351 A1 | | 2/2007 | Fleischman et al. |
| 2008/0114354 A1 | | 5/2008 | Whayne et al. |
| 2008/0114355 A1 | | 5/2008 | Whayne et al. |
| 2009/0137870 A1 | * | 5/2009 | Bakos ...................... A61B 1/01 |
| | | | 600/116 |
| 2009/0275972 A1 | * | 11/2009 | Uemura ............. A61B 17/3421 |
| | | | 606/192 |
| 2009/0281500 A1 | | 11/2009 | Acosta et al. |
| 2011/0230906 A1 | * | 9/2011 | Modesitt .................. A61B 1/04 |
| | | | 606/185 |
| 2012/0088968 A1 | * | 4/2012 | Gambhir ............... A61M 25/09 |
| | | | 600/106 |
| 2015/0182205 A1 | | 7/2015 | Millard |
| 2016/0331207 A1 | | 11/2016 | Ibrahim et al. |

OTHER PUBLICATIONS

U.S. Appl. No. 15/154,714, filed May 13, 2016 in the name of Ibrahim et al. Non-Final Office Action mailed Sep. 25, 2018.

U.S. Appl. No. 15/154,714, filed May 13, 2016 in the name of Ibrahim et al., Final Office Action mailed May 7, 2019.

* cited by examiner

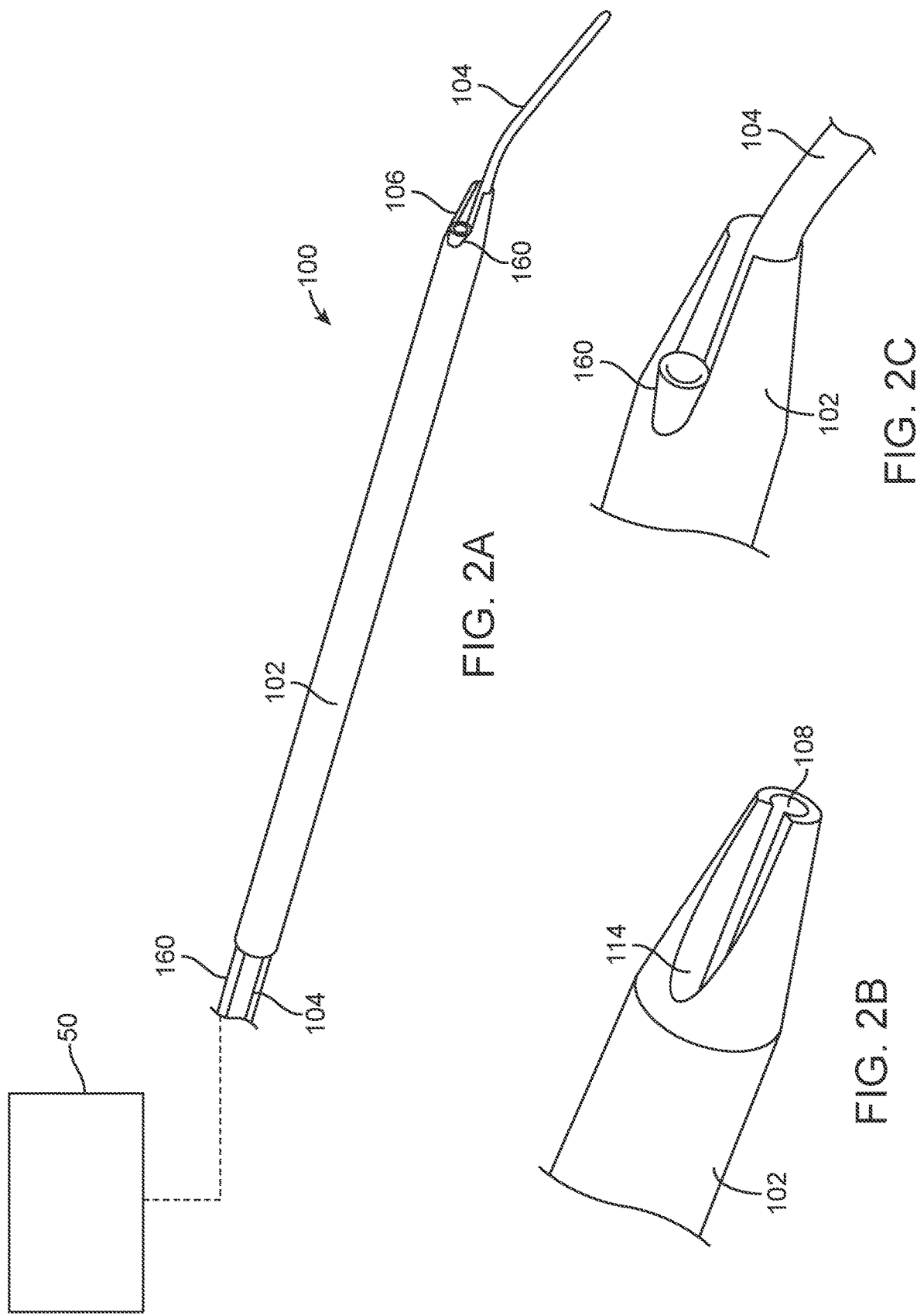

ACCESS VISUALIZATION SYSTEMS

CROSS-REFERENCE TO RELATED APPLICATIONS

This application is a divisional of U.S. Non-Provisional patent application Ser. No. 15/154,714 filed on May 13, 2016 which claims priority to U.S. Provisional Patent Application No. 62/160,997 filed on May 13, 2015, the contents of which is incorporated herein by reference in their entireties.

BACKGROUND OF THE INVENTION

Methods and devices for access devices to allow improved access in preparation for performing surgical procedures or intervention in areas where collateral damage to sensitive tissue or organs can easily occur. For example, electrophysiologists or interventional cardiologists generally perform procedures under fluoroscopic guidance. However, issues arise when physician access the pericardial space because of their limited viewing capabilities under fluoroscopic guidance.

Scope based surgical tools (e.g., elongated cannula/tubular devices that allow viewing of internal body tissues) provide surgeons with an ability to view a surgical site through a lens/fiber optic/camera of the scope and also provide an ability to access the surgical site through a working channel of the tool. In some cases, a scope permits the surgeon to access internal body tissue by passing the scope through a small diameter opening, port, or trocar placed in a surface of the body. For convenience, the present disclosure makes reference an endoscope as a scope-based device. However, the inventive devices and methods described herein specifically include the use of any number of scope based devices generally similar to an endoscope; for example, any type of rigid or flexible tube with or without a light delivery system and a visualization source that transmits an image to the viewer, and (optionally) a working channel or lumen that permits delivery of an additional device through the scope.

In many surgical procedures, the surgeon must also dissect tissue to gain access to the intended target site. For example, U.S. Pat. No. 5,205,816 (the entirety of which is incorporated by reference) teaches a simple blunt dissector having a cannulated single lumen device with a mandrel inserted into the device for carrying a simple textured cloth that provides a textured surface. However, such basic devices are used in addition to the scopes that are used for such minimally invasive procedures. The additional blunt dissector requires an additional entry port or must be exchanged with other tools that are advanced through the entry site. In addition, a physician must manipulate a scope as well as the blunt dissection device.

Increasingly, scopes are being adapted to assist in the dissection of tissue to eliminate the need for an additional dissection device. Clearly, doing so reduces the number of devices that a physician must manipulate in the surgical area as well as the number of devices that are advanced through the body opening/port/incision. Many conventional devices rely upon balloon-type structures for dissection of tissue via expansion of the balloon or close-ended obturator-type structures that dissect via dilation via insertion of the closed end.

For example, U.S. Pat. No. 6,989,018 to Fogarty et al. (the entirety of which is incorporated by reference herein) discloses a balloon dissection apparatus having an elongate balloon that performs the tissue dissection. However, because this dissection relies upon somewhat uncontrollable expansion of the balloon (as the internal balloon pressure increases), the physician typically has less control over the amount of tissue dissection as compared to using a non-expanding structure to physically dissect tissue.

While obturator type devices avoid the problems with somewhat unpredictable dissection via balloon expansion, such devices are still not optimal. For example, U.S. Pat. Nos. 6,592,604; 6,752,756; and 7,001,404 (the entirety of each patent incorporated by reference herein) describe tissue dissection devices having with closed ends (where such ends act as obturators). The closed ends are generally translucent to allow for visualization therethrough. Yet, dissection of tissue occurs via dilation of the tissue using the closed end. U.S. Pat. No. 7,300,448 (the entirety of which is incorporated by reference herein) discloses a combination balloon dissector having an obturator associated with the balloon dissector assembly.

In any event, the balloon dissection or dissection via obturator dilation as described above do not provide the physician with the ability to tease or loosen adjoining tissue for a more controlled dissection of tissue.

Accordingly, there is a need for improved methods and devices that permit visualization to allow the physicians more comfort in performing various procedures while minimizing the risk of collateral damage to tissue or to the tissue being dissected/dilated.

SUMMARY OF THE INVENTION

In one variation, the present method of solving this problem is using an integrated endoscope system, which provides electrophysiologists or interventional cardiologists visualization of the access procedure. The benefit of the integrated endoscope system is that it provides a safe and easy seamless passage for entering the pericardial space with visualization to minimize trauma to the heart. The integrated endoscope system may provide access to the pericardial space by percutaneous pericardial access.

The improved methods and devices described herein offer improved access to tissue regions within the body, especially those organs in the thoracic cavity. However, the devices and methods have applicability to any region in the body apart from the thoracic cavity.

In a first variation, the present system includes an endoscope configured to provide remote visualization; a dilator member having a proximal portion, a distal portion, a distal end, and a dilator passage extending from the proximal portion through the distal end, the dilator member further comprising a dilation surface located about an outer surface at the distal portion, where a profile of the dilator surface increases in size along a proximal direction such that insertion of the dilator portion in an opening in tissue dilates the tissue; a guide tube extending from the distal end of the dilator member and having a guide passage in fluid communication with the dilator passage; and where the endoscope is advanceable through the guide tube passage such that a visualization end of the endoscope can be repositioned within the guide tube.

The variation of the above system can further include a second endoscope extending through the dilator member and radially offset from the guide tube. In some examples, the second endoscope comprises a second visualization end exiting at a dilation surface of the dilator member.

Variations of the system can include a configuration where the dilator member is slidable relative to the guide member.

In order to aid in visualization using the scopes, any portion of the system can be transparent. Similarly, additional variations include portions of the system that are opaque.

The guide member described herein can be removable from the dilator member or fixed to the dilator member.

In another variation, the present disclosure includes a dilation system for use with an endoscope configured to provide remote visualization, the endoscope comprising a visualization end located at a distal portion, the dilation system comprising: a dilator member having a proximal portion, a distal portion, a distal end, and a dilator passage extending from the proximal portion through the distal end, the dilator member further comprising a dilation surface located about an outer surface at the distal portion, where a profile of the dilator surface increases in size along a proximal direction such that insertion of the dilator portion in an opening in tissue dilates the tissue; a guide tube extending from the distal end of the dilator member and having a guide passage in fluid communication with the dilator passage; and where the endoscope is advanceable through the guide tube passage such that the visualization end of the endoscope can be repositioned within the guide tube.

In an additional variation, the present disclosure includes methods for placement of an endoscope adjacent to a target site. In one example such a method comprises positioning an access device adjacent to an opening in tissue, the access device comprising a guide tube and a dilator member, where the guide tube is coupled to at a distal end of the dilator member; inserting the guide tube of the access device within the opening in tissue; dilating the opening in tissue by advancing the dilator member of the access device through the opening in tissue; and imaging the target site using the endoscope while the endoscope is positioned through the dilator member.

The method can further include visualizing using the endoscope while inserting the guide tube of the access device within the opening.

In an additional variation, the method includes an opening in tissue which comprises an opening in a pericardial space.

In certain variations, the method includes a guide tube is transparent and further comprising visualizing through a wall of the guide tube using the endoscope. Alternatively or in combination, where the dilator can be transparent and the method further comprises visualizing through a wall of the guide tube using the endoscope.

In some variations of the method and devices, the endoscope is affixed to the dilator member and where imaging the target site using the endoscope while the endoscope is positioned through the dilator member comprises repositioning the dilator member to reposition the endoscope.

Variations of the method further include advancing a second endoscope through the guide tube.

The present methods can include the use of any conventional device to assist in accessing the body. For example, the methods can further include advancing a guidewire through the opening in tissue and where inserting the guide tube comprises advancing the guide tube over the guidewire.

Variations of the access device and procedures described herein include combinations of features of the various embodiments or combination of the embodiments themselves wherever possible.

BRIEF DESCRIPTION OF DRAWINGS

FIGS. 2A to 2C illustrate another variation of a dilation system that can optionally be integrated with an endoscope external to a guide tube of the system.

DETAILED DESCRIPTION

Methods and devices described herein provide for improved access of regions within the body using remote visualization, such as endoscopes. The improved methods and devices described herein offer improved access to tissue regions within the body, especially those organs in the thoracic cavity. For purposes of illustration, the following example discusses the methods and devices as used when a physician accesses a pericardial space within a thoracic cavity of an individual, however, the devices and methods have applicability to any region in the body where the benefits of the methods and procedures can assist in the procedure.

Scope based surgical tools (e.g., elongated cannula/tubular devices that allow viewing of internal body tissues) provide surgeons with an ability to view a surgical site through a lens/fiber optic/camera of the scope and also provide an ability to access the surgical site through a working channel of the tool. In some cases, a scope permits the surgeon to access internal body tissue by passing the scope through a small diameter opening, port, or trocar placed in a surface of the body. For convenience, the present disclosure makes reference an endoscope as a scope-based device. However, the inventive devices and methods described herein specifically include the use of any number of scope based devices used for remotely viewing an area of tissue generally similar to an endoscope; for example, any type of rigid or flexible tube with or without a light delivery system and a visualization source that transmits an image to the viewer, and (optionally) a working channel or lumen that permits delivery of an additional device through the scope.

Figure 1A:
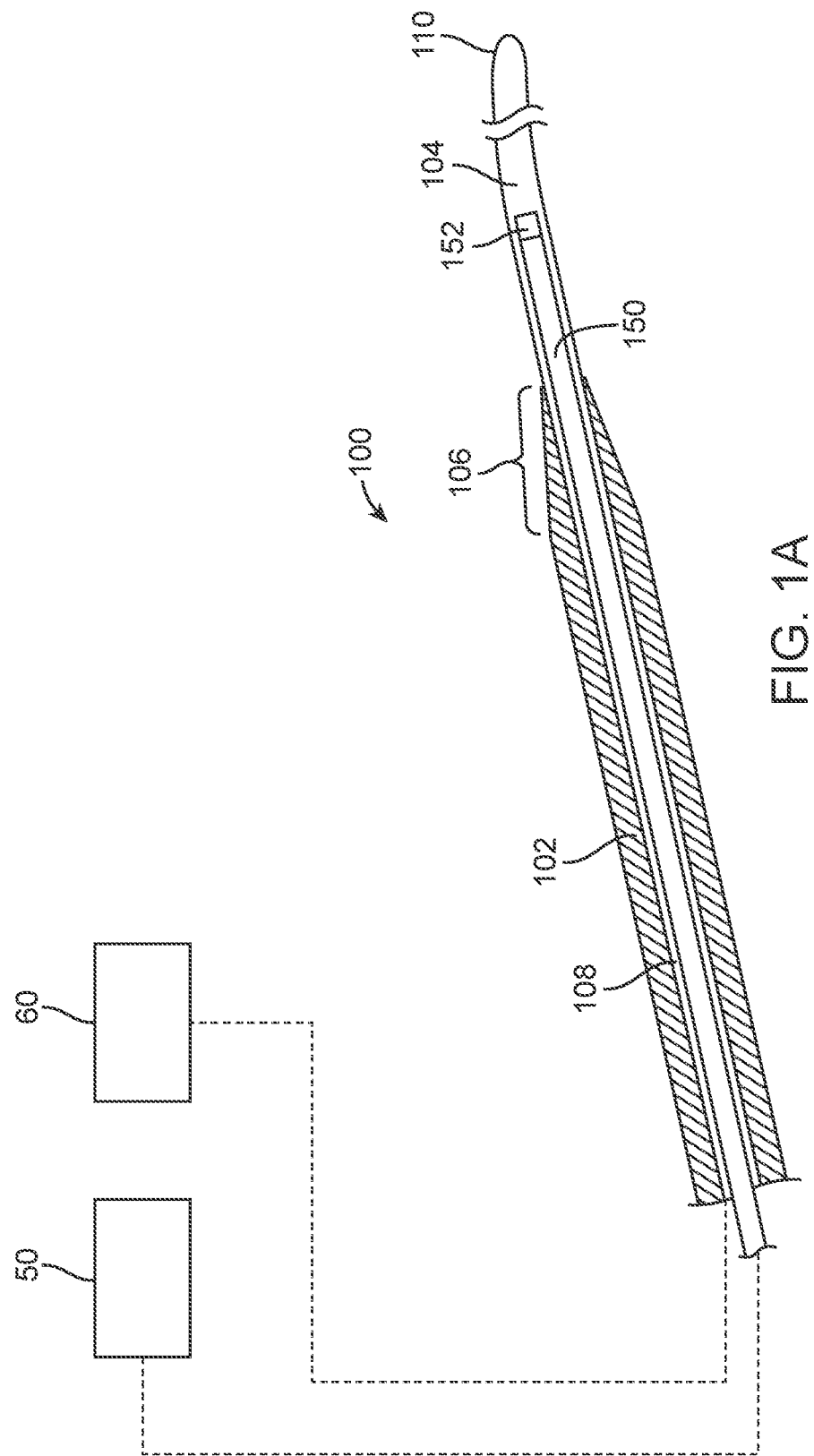
FIG. 1A illustrates a first variation of an endoscopic system or dilation system \ (when the endoscope is a stand-alone added component).

FIG. 1A illustrates a first variation under the present disclosure of an endoscopic system 100 or dilation system 100 (when the endoscope is a stand-alone added component). As illustrated the system 100 includes a dilator member 102 having a distal dilation surface 106 and a dilator passage 108 extending therethrough. A guide tube 104 extends distally from the dilator passage 108 allowing for an endoscope 150 to be advanced therethrough. The end 110 of the guide tube 104 can be open or can be closed. In the illustrated variation, the end 110 of the guide tube 104 is configured to be atraumatic.

The components of the system 100 can include any conventional features useful for medical devices and/or procedures. For example, the system 100 can be configured for coupling to a visual display 50 for viewing the images transmitted/relayed from the visualization end 152 of the endoscope 150. In addition, the system can include any number of auxiliary fixtures (such as a fluid source, vacuum source, controller for electrodes/pacing, etc.) In addition, the guide tube 104 and/or dilator member 102 can have steering capabilities or pre-set shapes to assist in navigating the respective component within tissue.

Figure 1B:
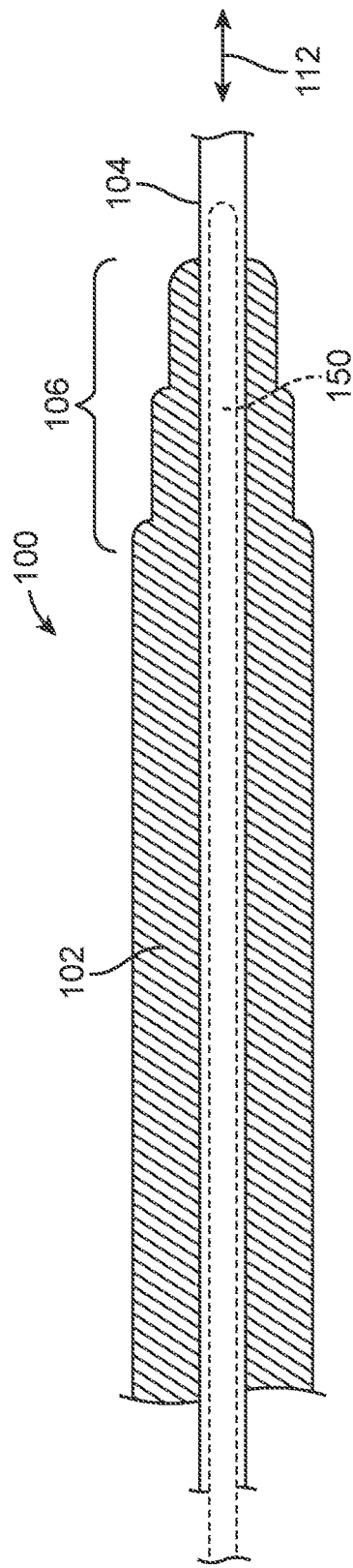
FIGS. 1B and 1C illustrate additional variations of systems for navigation of an endoscopic device.
Figure 1C:
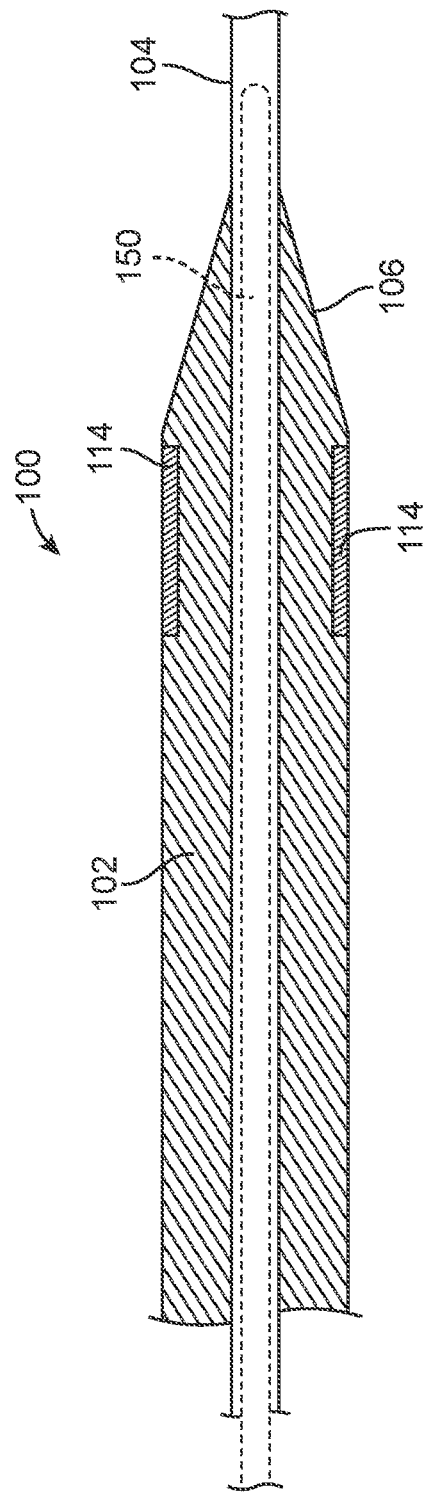

FIGS. 1B and 1C illustrate additional variations of systems 100 for navigation of an endoscopic device 150. As shown, the guide tube 104 can optionally extend through the length of the dilator 102 and can optionally move relative to the dilator 102 as indicated by arrows 112. Furthermore, the dilation surface 106 of the variation shown in FIG. 1B, can be stepped rather than conical (as shown in FIG. 1A). However, any atraumatic shape can be used for the dilation surface 106. FIG. 1C also illustrates a dilator 102 having an additional dilation feature 114 such as a distensible or non-distensible balloon 114.

In any of the variations of the systems described herein, one or more of the components can be configured to assist or improve visualization of a target site by the endoscope. For example, the dilator and/or the guide sheath can be fabricated from opaque or transparent materials. Alternatively, or in combination, the dilator and/or guide tube can include a transparent window that assist in visualization by the endoscope.

FIGS. 2A to 2C illustrate another variation of a dilation system 100 (that can optionally be integrated with an endoscope 160). In this variation, a dilator 102 includes a guide tube 100 extending therethrough with the distal end of the guide tube 110 extending beyond the dilation surface 106 of the dilator 102. However, this variation also includes an internal endoscope 160 that is adjacent to the guide tube 110. Such a configuration allows the internal endoscope 160 to provide an unobstructed view (via the display 50) allowing the physician to visualize the tissue adjacent to the dilation surface 106 as the dilator advances.

FIGS. 2B and 2C illustrate the end of the dilator 102 shown in FIG. 2A. As shown in FIG. 2B, the dilator 102 can include a scalloped opening or one where there are two passages that are parallel. The passages 108 and 114 can be joined (as shown in FIG. 2B) or separated (such as those found in a multi-lumen tube). Additional variations of the dilator opening can include various other shapes. However, in the illustrated variation, the opening 114 provides space for the internal scope (as shown in FIG. 2C). Similar to the variation shown in FIG. 1A, the dilator and/or guide tube may be composed of either opaque or transparent materials. The internal scope 160 can be affixed to the dilator as shown in FIG. 2C. Alternatively, the scope 160 can be moveable relative to the dilator 102.

Figure 3:
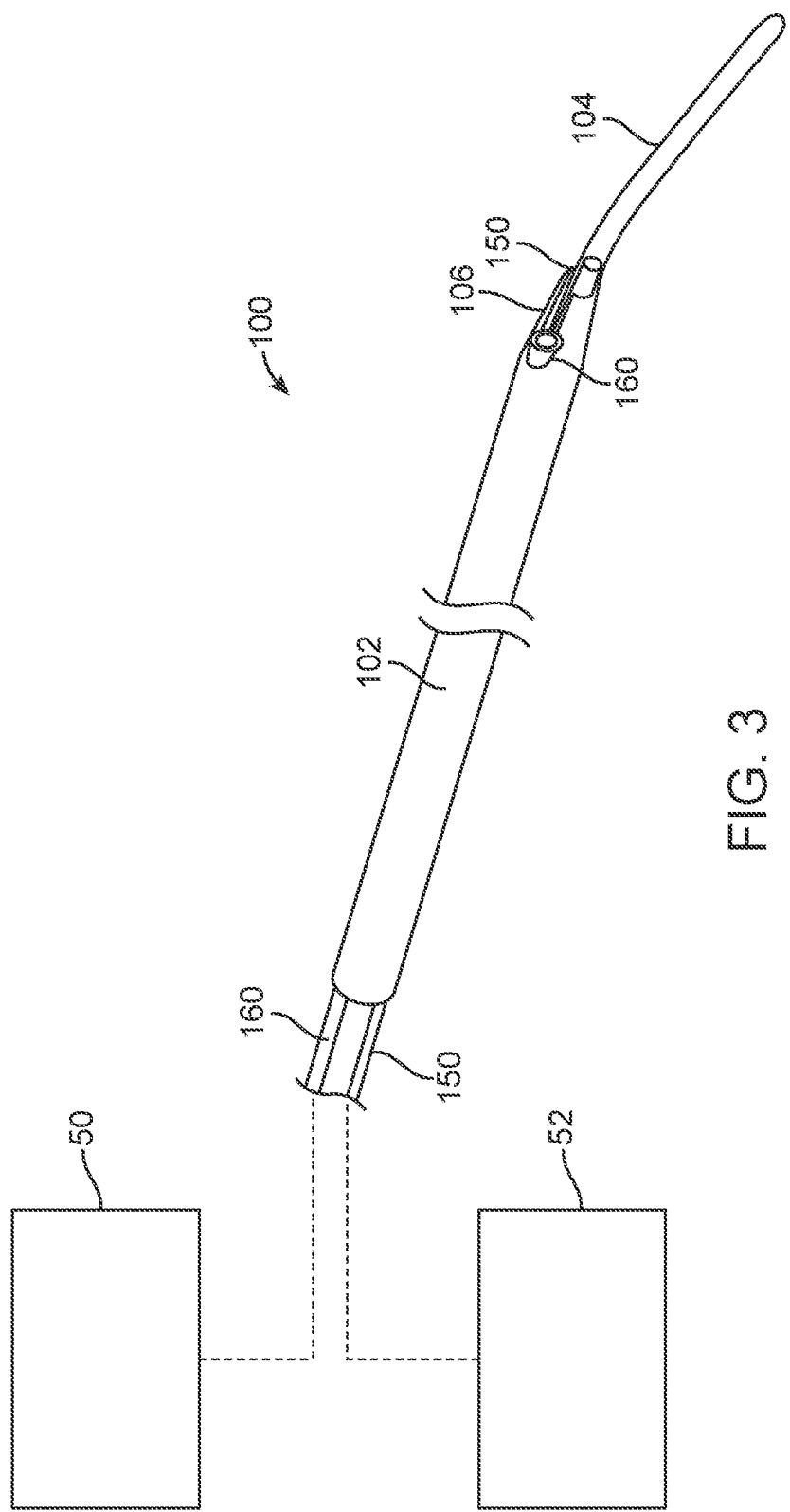
FIG. 3 shows another variation of the system similar to that shown in FIG. 2A. In this variation, the system includes two scopes.

FIG. 3 shows another variation of the system 100 similar to the one shown in FIG. 2A. In this variation, the system 100 includes two scopes 150, 160. As noted above, as the dilator member 102 includes an internal scope 160 (either fixed or moveable within the dilator member 102). An additional scope 150 can be advanced through the guide member 104 as discussed above with respect to FIG. 1A. The variation shown in FIG. 3 can include an additional monitor/display 52. Alternatively, or in combination, the image generated by both scopes 150, 160 can be projected on both monitors or a single monitor.

FIGS. 4A-4E illustrates a variation of a process of positioning or placing an endoscope using the system described herein. As show in FIG. 4A, a variation of the procedure uses minimal incisions 10 and 12 to access the chest cavity. Alternatively, or in combination, an incision 14 can be made that requires traversing a diaphragm of the individual 1 in order to access the thoracic cavity. In some variations, the procedure can be performed percutaneously. Again, alternate variations of the method can occur in an open surgical procedure or with any number of surgical incisions. The integrated system can be inserted into the patient through any number of conventionally known access methods.

Figure 4A:
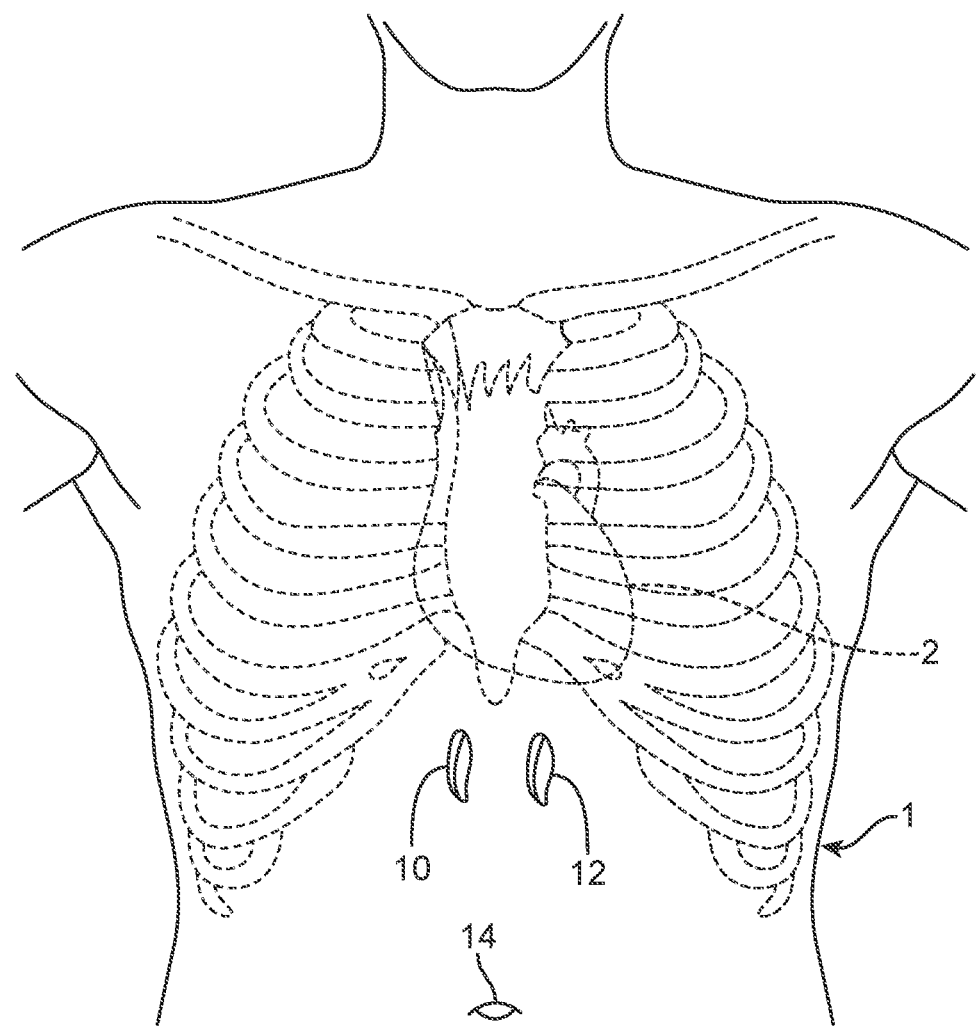
FIGS. 4A-4E illustrates a variation of a process of positioning or placing an endoscope using the system described herein
Figure 4B:
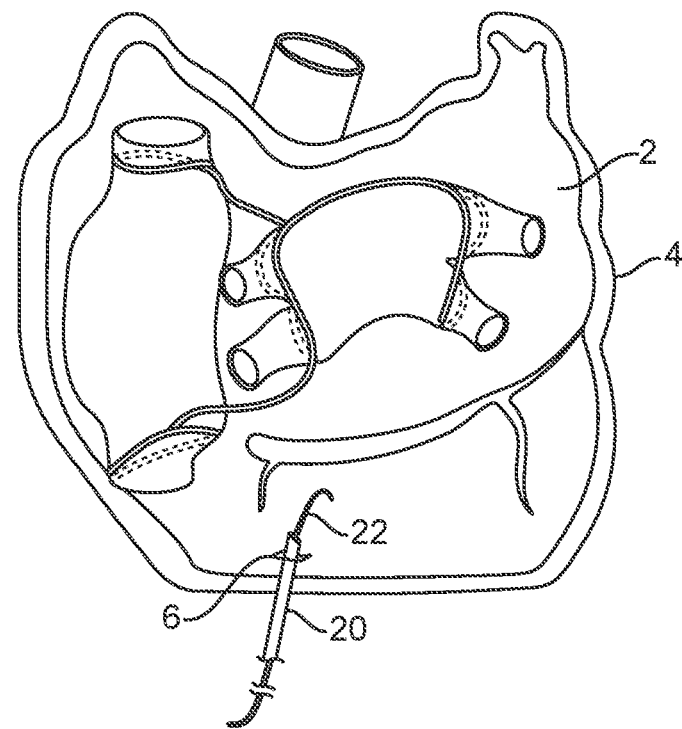

FIG. 4B illustrates a heart 4 surrounded by a pericardium 4 in order to demonstrate an example of a process for placement of a scope using the system described herein. Any number of commercial devices can be used in conjunction with the systems described herein. For example, a commercially available dilator (e.g., for renal applications) can optionally be inserted be to provide access to the pericardium 4. As shown, a physician can percutaneously insert a needle 20 into the pericardial sac 4 via an initial pericardial incision or entry point 6. Next, under fluoroscopic guidance (optional), a guidewire 22 can be delivered through the needle 20 into the pericardial space. In another variation, a physician can use an expandable cannula to insert the integrated system disclosed herein. The physician can use this expandable cannula with an initial insertion profile to minimize the size the pericardial opening to enter the pericardium. Once inserted, the physician expands the expandable cannula to allow for insertion of any of the disclosed integrated endoscope systems.

Figure 4C:
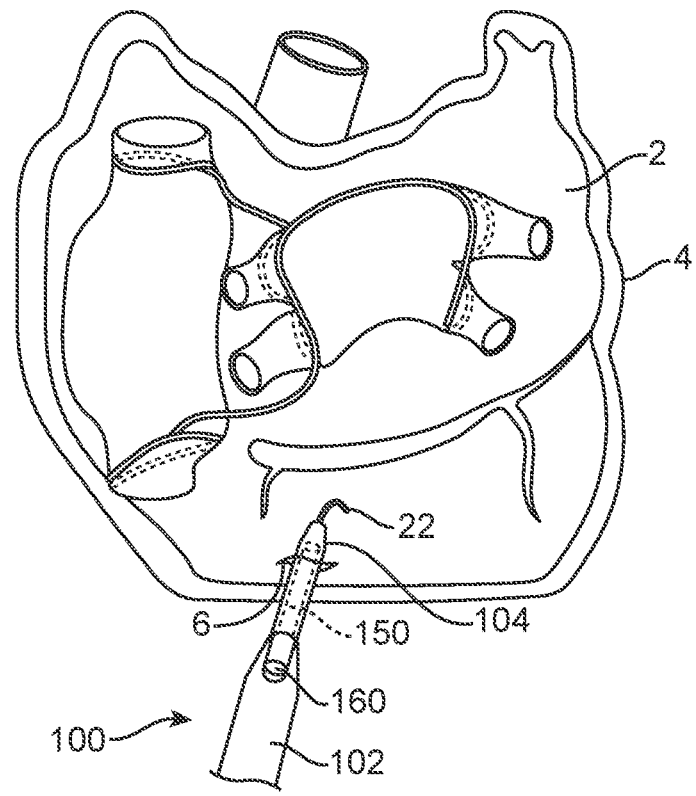

FIG. 4C illustrates the state where the physician removes the needle 20 leaving the guidewire 22 in place. Next, the physician introduces a system 100 adjacent to the site and advances a guide tube 104 over the guidewire 22 through the pericardial incision 6 and into the pericardial space. As illustrated, a first scope 150 can optionally be inserted through the guide tube 104 to assist the physician by allowing for visualization of the in the pericardial space that is otherwise obscured by the pericardium 4. In some variations of the device the guidewire 22 must be removed to advance the scope 150. In alternate variations, the guide tube 104 is configured to accommodate both a scope and guidewire. Additionally or alternatively, variations of the system including an internal scope 160 allow the physician visual access to the region adjacent to the distal end of the dilator member 102 and guide tube 104.

Figure 4D:
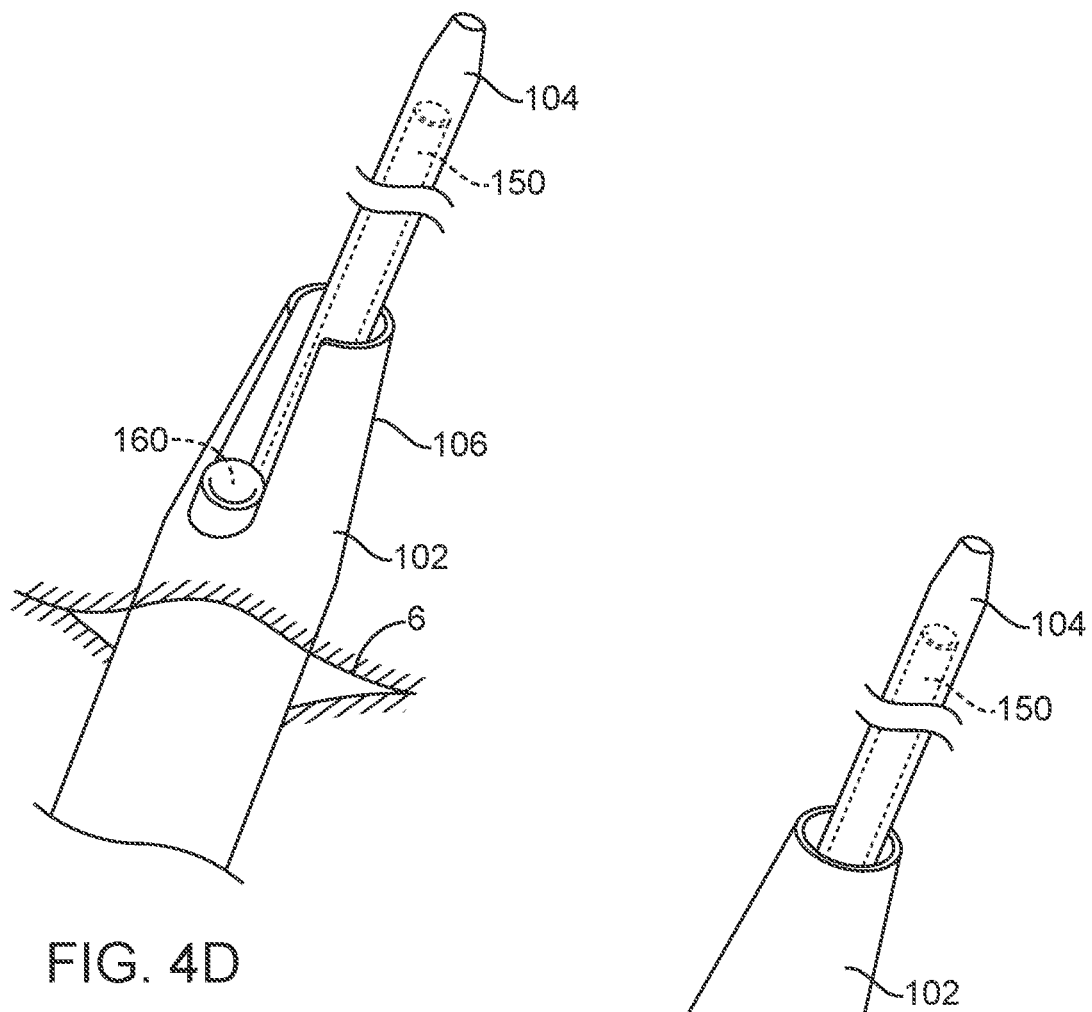
Figure 4E:
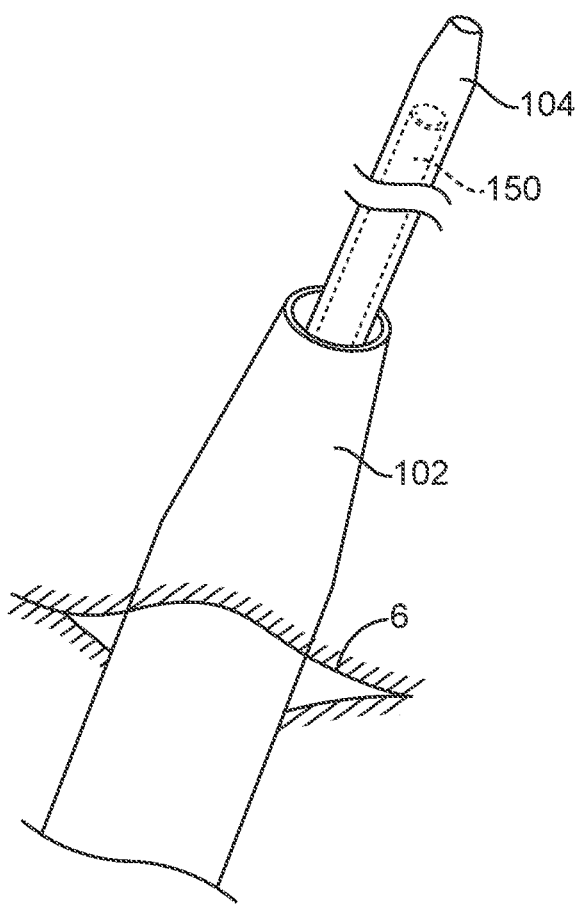

FIGS. 4D and 4E illustrate examples of a dual scope system and a single scope system, respectively. As noted above for those variations, as shown in FIG. 4D, a physician can use an internal scope 160 that is positioned adjacent to a dilation surface 106 of the dilator member 102 for visualization. The physician also has the option of using a second scope 150 that passes through the guide tube 104. FIG. 4E illustrates an example of the system where the scope 150 is positioned through the guide tube 104. As noted in either of FIGS. 4D and 4E, the physician can advance the dilator member 102 to further dilate the opening 6.

Once the opening is dilated and the physician inspects the area of interest, the physician can then advance an additional cannula or a hollow sheath the dilator member of the system. Alternatively, a commercial dilator can be advanced over the dilator member 102 to permit removal of the dilator member 102 and system to prepare the site for further surgical devices.

For example, integrated vacuum coagulation probes provided by AtriCure, Ohio, are examples of devices that can be inserted through the openings provided by the systems described above. Such devices are capable of heating the soft tissue until achieving irreversible injury making the soft tissue non-viable and unable to propagate electrical impulses, mutate, or reproduce. These integrated vacuum coagulation probe embodiments may be in conjunction with the access devices described herein to treat atrial fibrillation, ventricular tachycardia or other arrhythmia substrate, or eliminating cancer in lung, or other soft thoracic tissue by destroying target cells.

Examples of such probes are disclosed in commonly assigned U.S. publications and patents: US20060009762A1 entitled VACUUM COAGULATION PROBE FOR ATRIAL FIBRILLATION TREATMENT; US20060200124A1 entitled VACUUM COAGULATION PROBES; US20060206113A1 entitled METHODS FOR COAGULATION OF TISSUE; US20060235381A1 entitled VACUUM COAGULATION PROBES; US2006-0293646A1 entitled VACUUM COAGULATION & DISSECTION PROBES; US20070043351A1 entitled VACUUM COAGULATION PROBES; US20080114354A1 entitled VACUUM COAGULATION PROBES; US20080114355A1 entitled VACUUM COAGULATION PROBES; and U.S. Pat. No. 6,893,442 entitled VACUUM COAGULATION PROBE FOR ATRIAL FIBRILLATION TREATMENT; U.S. Pat. No. 7,063,698 entitled VACUUM COAGULATION PROBES; the entirety of each of which is hereby incorporated by reference.

Although the present methods and devices have been described in terms of the embodiments above, numerous modifications and/or additions to the above-described preferred embodiments would be readily apparent to one skilled in the art. It is intended that the scope of the present inventions extend to all such modifications and/or additions and that the scope of the present inventions is limited solely by the claims of the invention.

What is claimed is:

1. A method for placement of an endoscope adjacent to a target site, the method comprising:

positioning an access device adjacent to an opening in tissue to enter a pericardial space, the access device comprising a guide tube, a dilator member, and the endoscope, wherein the endoscope is integrated within the access device;

the dilator member having a proximal portion, a distal portion, a distal end, and a dilator passage extending from the proximal portion through the distal end, the dilator member further comprising a dilation surface being atraumatic and located about an outer surface at the distal portion, where a profile of the dilator surface increases in size along a proximal direction such that insertion of the dilator member in an opening in tissue dilates the tissue, the guide tube coupled to the dilator member and extending through the dilator passage, wherein the guide tube is configured to move axially relative to the dilator member, the guide tube further comprising an atraumatic end;

inserting the guide tube within the opening in tissue leading with the atraumatic end, the guide tube extending from the distal end of the dilator member and having a guide passage within the dilator passage, where the guide tube is independently manipulable from the endoscope when the guide tube is advanced distally through the dilator passage and past the distal end of the dilation member, where the guide tube maintains a tubular shape when advanced through the dilator passage;

dilating the opening in tissue by advancing the dilator member over the guide tube and toward the atraumatic end through the opening in tissue; and imaging the target site using the endoscope while the endoscope is positioned through the dilator member.

2. The method of claim 1, further comprising visualizing using the endoscope while inserting the guide tube within the opening.

3. The method of claim 1, where the guide tube is transparent and further comprising visualizing through a wall of the guide tube using the endoscope.

4. The method of claim 1, where the dilator member is transparent and further comprising visualizing through a wall of the guide tube using the endoscope.

5. The method of claim 1, further comprising advancing the endoscope through the dilator member.

6. The method of claim 5, further comprising advancing the endoscope through the guide tube.

7. The method of claim 1, where imaging the target site using the endoscope comprises repositioning the dilator member to reposition the endoscope.

8. The method of claim 7, further comprising advancing a second endoscope through the guide tube.

9. The method of claim 1, further comprising advancing a guidewire through the opening in tissue and where inserting the guide tube comprises advancing the guide tube over the guidewire.

10. The method of claim 1, where the dilator member is moveable over guide tube.

11. The method of claim 10, further comprising removing the dilator member from the guide tube and advancing a second dilator member over the guide tube.

12. The method of claim 1, further comprising a distensible or non-distensible balloon.

13. The method of claim 1, wherein the guide tube is flexible.

14. The method of claim 1, wherein the dilator member is slidable relative to the guide tube.

15. The method of claim 1, wherein the distal end of the guide tube is tapered.

* * * * *